United States Patent
Vlekken et al.

(10) Patent No.: US 12,025,514 B2
(45) Date of Patent: Jul. 2, 2024

(54) METHOD AND DEVICE FOR MEASURING FORCE AND SHAPE

(71) Applicants: FBGS TECHNOLOGIES GMBH, Jena (DE); FBGS INTERNATIONAL NV, Geel (BE)

(72) Inventors: Johan Vlekken, Diepenbeek (BE); Bram Van Hoe, Ghent (BE); Eric Lindner, Jena (DE)

(73) Assignees: FBGS TECHNOLOGIES GMBH, Jena (DE); FBGS INTERNATIONAL NV, Geel (BE)

( * ) Notice: Subject to any disclaimer, the term of this patent is extended or adjusted under 35 U.S.C. 154(b) by 808 days.

(21) Appl. No.: 16/623,224

(22) PCT Filed: Jun. 15, 2018

(86) PCT No.: PCT/EP2018/066034
§ 371 (c)(1),
(2) Date: Dec. 16, 2019

(87) PCT Pub. No.: WO2018/229288
PCT Pub. Date: Dec. 20, 2018

(65) Prior Publication Data
US 2020/0191669 A1 Jun. 18, 2020

(30) Foreign Application Priority Data
Jun. 15, 2017 (EP) ..................... 17176287

(51) Int. Cl.
*G01L 1/24* (2006.01)
*A61B 5/06* (2006.01)
(Continued)

(52) U.S. Cl.
CPC .............. *G01L 1/246* (2013.01); *A61B 5/065* (2013.01); *A61B 17/3403* (2013.01);
(Continued)

(58) Field of Classification Search
CPC .. G01L 1/246; A61B 5/065; A61B 2034/2061
See application file for complete search history.

(56) References Cited

U.S. PATENT DOCUMENTS

2009/0324161 A1 12/2009 Prisco
2011/0274387 A1* 11/2011 Arkwright ............. G01B 11/18
385/13

(Continued)

FOREIGN PATENT DOCUMENTS

EP 2780681 A1 9/2014
WO WO-03076887 A1 * 9/2003 ......... G01D 5/35316

OTHER PUBLICATIONS

International Search Report and Written Opinion from PCT Application No. PCT/EP2018/066034, dated Sep. 14, 2018.

*Primary Examiner* — Colin T. Sakamoto
*Assistant Examiner* — Tommy T Ly
(74) *Attorney, Agent, or Firm* — Workman Nydegger

(57) ABSTRACT

An optical system comprises a multicore fiber comprising at least two cores of which each core comprises at least one Fiber Bragg Grating. The optical system also comprises a force transducing element being bendable in one or more directions and being fixed to the multicore fiber so as to transduce force applied to the force transducing element to the multicore fiber, resulting into a bending and/or compression and/or tension of the multicore fiber. The multicore fiber is connectable or connected to a measurement system for optically measuring the response of at least one Fiber Bragg Grating, for each of at least 2 cores of the multicore fiber, as a result of the multicore fiber bending and/or compression and/or tension for deriving a characteristic of the force acting on the position of the force transducing element of the optical system.

18 Claims, 1 Drawing Sheet

(51) Int. Cl.
*A61B 17/34* (2006.01)
*A61B 34/20* (2016.01)
*A61B 34/30* (2016.01)
*A61M 25/01* (2006.01)

(52) U.S. Cl.
CPC .............. *A61B 34/20* (2016.02); *A61B 34/30* (2016.02); *A61M 25/0105* (2013.01); *A61B 17/3468* (2013.01); *A61B 2034/2061* (2016.02); *A61M 2025/0166* (2013.01)

(56) References Cited

U.S. PATENT DOCUMENTS

| | | | |
|---|---|---|---|
| 2014/0053654 A1* | 2/2014 | Rogge | G01L 1/246 |
| | | | 73/800 |
| 2014/0142607 A1* | 5/2014 | Cage | A61B 17/22 |
| | | | 606/185 |
| 2015/0029511 A1* | 1/2015 | 'T Hooft | G01B 11/16 |
| | | | 356/477 |
| 2017/0196479 A1* | 7/2017 | Liu | A61B 5/6852 |
| 2017/0303824 A1* | 10/2017 | Schlesinger | A61B 1/018 |
| 2018/0136058 A1* | 5/2018 | Singer | G01L 3/12 |
| 2018/0368934 A1* | 12/2018 | Van Der Linde | |
| | | | A61M 25/0053 |
| 2020/0056907 A1* | 2/2020 | Godfrey | G01D 5/3538 |
| 2020/0155073 A1* | 5/2020 | Hwang | A61B 90/06 |

* cited by examiner

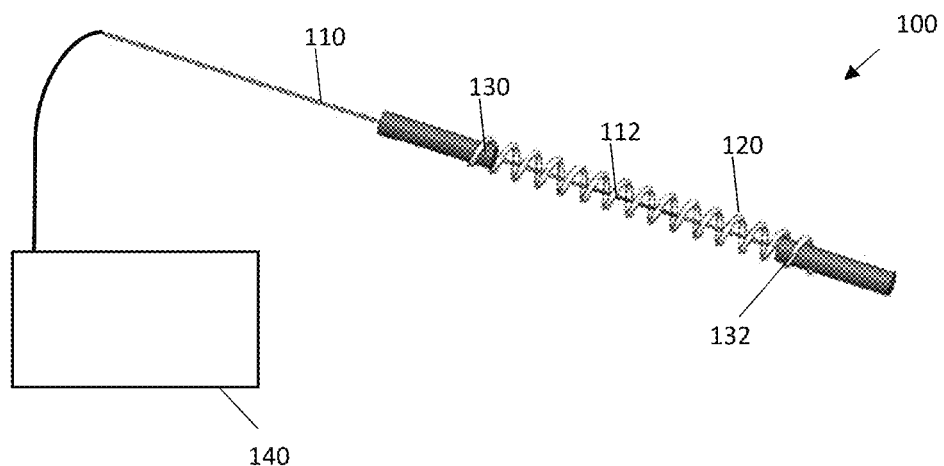

METHOD AND DEVICE FOR MEASURING FORCE AND SHAPE

FIELD OF THE INVENTION

The present invention relates to the field of force sensing. More particularly, the present invention relates to a system and method for sensing force based on a multicore fiber comprising a Fiber Bragg Grating and a force transducing element.

SUMMARY OF THE INVENTION

It is an object of embodiments of the present invention to provide good methods and systems for sensing force, e.g. applicable for deriving information on forces applied to a medical device, and optionally shape and/or curvature of the medical device.

The object is obtained by a system and/or method according to the present invention.

The present invention relates to an optical system, the optical system comprising a multicore fiber comprising at least two cores of which each core comprises at least one Fiber Bragg Grating, a force transducing element being bendable in one or more directions and being fixed to the multicore fiber so as to transduce force applied to the force transducing element to the multicore fiber, resulting into a bending and/or compression and/or tension of the multicore fiber, the multicore fiber being connectable or connected to a measurement system for optically measuring the response of at least one Fiber Bragg Grating, for each of at least 2 cores of the multicore fiber, as a result of the multicore fiber bending and/or compression and/or tension for deriving a characteristic of the force acting on the position of the force transducing element of the optical system. It is an advantage of embodiments of the present invention that accurate force sensing can be performed using the optical system. The force may be a one or more dimensional force.

The force transducing element may be a spring means. It is an advantage of embodiments of the present invention that a system can be used that is easy to manufacture.

The force transducing element may be a compressive spring means.

The compressive spring can be designed such that it has no preferential bending direction.

It is an advantage of embodiments of the present invention that the system allows for measuring lateral forces with a sensitivity that is independent of the direction wherein the force is applied. In other words, embodiments of the present invention encompass optical systems having, at the position of the force transducing element, a non-preferential bending, thus allowing more accurate measurements of the force.

The force transducing element and the multicore fiber may be fixed to each other such that the multicore fiber is under pretension when no external force, external to the force transducer, is applied to the system. It is an advantage of embodiments of the present invention that, when the multicore fiber is under pretension, buckling of the fiber in the force transducing element can be avoided. It is an advantage of embodiments according to the present invention that by connecting the fiber under pretension to a compressive spring or more generally a compressive force transducing element, the optical system can become more sensitive in compression. It is an advantage of embodiments according to the present invention that by using a compressive force transducing element, the force required, besides the force from the compressive force transducing element, for compressing the fiber can be smaller.

According to some embodiments, the fiber may, at the height of the force transducing element, be surrounded by the force transducing element or in other words, the fiber may pass through an open space in the force transducing element.

The force transducing element may be fixed to the multicore fiber at two fixation points such that the at least one Fiber Bragg Grating is positioned on the multicore fiber in between the two fixation points.

The force transducing element may be fixed along a length of the multicore fiber spanning at least the Fiber Bragg Grating(s).

The system may comprise a fixing means, such as for example but not limited to glue or glass solder material, between the force transducing element and the multicore fiber, wherein the force transducing element, the glue and the multicore fiber may be configured such that the multicore fiber is under pretension.

A stiffness of the force transducing element may be selected to dominate the stiffness of the host material wherein the force transducing element is integrated. It is an advantage of embodiments of the present invention that the stiffness at the location of the force transducing element is substantially not depending on structural elements surrounding the fiber and the force transducing element, since the other structural elements may change significantly with temperature (e.g. catheter tube). In this way, an optical system suitable for characterizing a force thereon can be obtained that is less sensitive to temperature variation.

Where reference is made to the stiffness, reference is made to at least one of the bending stiffness and/or compression stiffness and/or tension stiffness. In some embodiments, reference may be made to a combination of more or all of the bending stiffness, the compression stiffness and the tension stiffness.

The force transducing element properties may be adapted for obtaining/tuning the appropriate force sensitivity in a lateral and/or longitudinal direction of the multicore fiber. It is an advantage of embodiments of the present invention that force in a longitudinal direction as well as in a lateral direction on the multicore fiber can be tuned in the system.

The optical system may comprise said measurement system. It is an advantage of embodiments of the present invention that the system can be self contained. The measurement system may comprise an optical source for coupling radiation in one or more of the cores of the multicore fiber. The measurement system may comprise an optical detector for detecting radiation introduced earlier in the multicore fiber, for evaluating the response of the Fiber Bragg Grating(s) in the multicore fiber.

The measurement system may be configured for performing a calibration step whereby information regarding the status of the at least one Fiber Bragg Grating in the multicore fiber is obtained prior to an external force being applied. It is an advantage of embodiments of the present invention that accurate calibration of the optical system can be obtained.

The optical system may be a force sensing system. It is an advantage of embodiments of the present invention that accurate force information can be obtained from the system.

The multicore fiber may be a twisted multicore fiber whereby the cores, e.g. the outer cores, are twisted inside the cladding. Where in embodiments of the present invention reference is made to a twisted multicore fiber, reference is made to the outer cores being situated in a spiral or spiral-like shape around the centerline of the fiber. This has the advantage that the longitudinal strain response of the Fiber Bragg Gratings in the outer cores is different from the longitudinal strain response of the Fiber Bragg Gratings in the center core. As a consequence, the longitudinal force and temperature influences acting on the optical system, at the position of the force transducing element, can be discriminated from each other. This does however assume that the torsion or twist of the multicore fiber will be controlled. The force transducing element can therefore for example be adapted to have a high resistance against torsion so that the multicore fiber will not become twisted. Where in embodiments of the present invention reference is made to a high resistance against torsion, reference is made to the case whereby the effect of externally induced torsion forces influence the resulting measurement result less than 25%, e.g. less than 10% or e.g. less than 5%. Alternatively, the optical sensing element can be integrated into a host material (e.g. catheter) in such a way that it becomes protected by the host material for twisting at the position of the force transducing element, when an externally induced torsion force is applied to the host material (e.g. due to the contact with the catheter tip against a tissue). In one possible embodiment the host material may for example comprise a braid, limiting or preventing the optical sensing element from being twisted. Where in embodiments of the present invention reference is made to limiting from being twisted, reference is made to the case whereby an externally induced torsion force applied to the host material, results in a twist of the optical sensing element being less than 25%, e.g. less than 10% or e.g. less than 5% compared to the twist the optical sensing element would have seen when the same externally induced torsion force was directly applied to the optical sensing element without the host material.

In another configuration, the force transducing element may be adapted for further inducing a controlled twist to the multicore fiber when an external longitudinal force is induced. It may for example be a rotation spring.

The measurement system may be adapted for deriving temperature information from an optical characteristic influenced by twisting of the multi core fiber when a longitudinal force is induced. It is an advantage of embodiments of the present invention that a system can be obtained allowing to derive or take into account temperature information, so that more accurate determination of the force can be obtained. In other words, by applying an external longitudinal force, a twist or change in twist, may be induced in a multicore fiber. Since the central core will be twist insensitive this will result in a first source of information and since the sides will be twist sensitive this will result in a second source of information, both sources allowing to derive information regarding to the temperature as well as regarding to the force that is applied. The optical sensing element can further be integrated into a host material (e.g. catheter) in such a way that, aside from the twist induced due to the spring action, the optical sensing element is protected by the host material from externally induced torsion forces, e.g. due to the contact with the catheter tip against a tissue.

The force transducing element may be adapted for transducing a twist to the multicore fiber. The measurement system may be adapted for deriving a torsion of the multicore fiber and/or force transducing element. It is an advantage of embodiments of the present invention that information regarding torsion can be obtained.

The multicore fiber may have a preferential twist even if no external force is applied or present, in order to increase the torsion sensitivity and determine the direction of the torsion.

The optical system may provide force information regarding force applied on the catheter. It is an advantage of embodiments of the present invention that the system can be used for evaluating and/or controlling movement of the catheter.

In the optical system the multicore fiber furthermore may comprise at least one Fiber Bragg Grating positioned away from the force transducing element. This may assist in measuring at least one of the shape and/or the curvature of the catheter tip outside the force transducing element. This may also provide valuable information to control the force and understand the forces the transducer is seeing. For example, a force that suddenly drops because the catheter starts to buckle.

In some embodiments monitoring of the curvature and/or shape may be used for improving the calibration of the system and/or indicating when the system is in good use (e.g. when a small bending occurs in the catheter just before the force sensor, the sensor accuracy might become worse or the system might start to buckle). The system may for example be included in a feedback loop for providing information regarding the curvature and/or shape of a fibre in a plurality of applications.

The present invention also relates to a medical device comprising an optical system according to any of the previous claims, wherein the optical system provides force information regarding force applied on the medical device. The medical device may be any of a catheter, an introducer, a needle, a laparoscope, an endoscope or a robotic arm.

The present invention also relates to the use of an optical system as described above for evaluating and/or controlling forces applied to a catheter. The present invention may also relate to the use of an optical system as described above for contact force sensing.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

BRIEF DESCRIPTION OF THE DRAWINGS

FIG. 1 illustrates an optical system as can be used for force sensing according to an embodiment of the present invention.

The drawings are only schematic and are non-limiting. In the drawings, the size of some of the elements may be exaggerated and not drawn on scale for illustrative purposes. Any reference signs in the claims shall not be construed as limiting the scope. In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to an axial or longitudinal direction, reference is made to the length direction of the fiber. Where in embodiments of the present invention reference is made to a transversal direction, reference is made to directions perpendicular to the longitudinal direction.

Where in embodiments of the present invention reference is made to a multicore fiber, reference is made to a fiber comprising more than one core, e.g. 2 cores, e.g. 3 cores or even more cores, the cores being embedded in cladding material. The cores may be twisted.

In a first aspect, the present invention relates to an optical system for deriving a force applied to the optical system or to a system linked to or comprising such an optical system. In some embodiments, the system linked to the optical system or comprising the optical system may be a catheter, although embodiments of the present invention are not limited thereto. One application may be the determination of the force applied with/to the catheter during use, although embodiments are not limited thereto. According to the first aspect, the optical system comprises a multicore fiber comprising at least two cores of which each of the cores thereby comprises at least one Fiber Bragg Grating.

The optical system also comprises a force transducing element, such as for example a spring element. The force transducing element can be any elastic deformable element. The force transducing element is bendable in one or more directions. It is fixed to the multicore fiber so as to transduce force applied to the force transducing element to the multicore fiber, resulting into a bending and/or compression and/or tension of the multicore fiber. The multicore fiber is being connectable or connected to a measurement system for optically measuring the response of at least one Fiber Bragg Grating as a result of the multicore fiber bending and/or compression and/or tension for deriving a characteristic of the force on the optical system.

By way of illustration, embodiments of the present invention not being limited thereto, an exemplary optical system is described with reference to FIG. 1.

FIG. 1 illustrates an optical system 100. The optical system typically comprises a multicore optical fiber 110. The multicore optical fiber 110 may for example be a specially configured optical fiber with multiple single-mode cores sharing the same cladding. The different cores of the multicore fiber 110 may be individually addressed. The latter may for example be performed via a customized fiber optic fan-out element, but embodiments are not limited thereto. The cladding diameter may be any suitable diameter, such as for example but not limited to between 60 µm and 250 µm, e.g. 125 µm. The average core diameter may be of any suitable size such as for example but not limited to between 1 µm and 10 µm, e.g. 5 µm. In one arrangement, a single central core is surrounded by more outer cores. In some particular embodiments, one central core is applied and 3, 4, 5, 6 or 7 outer cores are provided. In some embodiments, the central core can also be avoided, so that there is no central core and only two or more outer cores. The outer cores may be symmetrically spaced. The outer cores may be positioned at a fixed position of the central core, although embodiments of the present invention are not limited thereto. The distance between the center and the outer cores may be any suitable size, e.g. may be about 35 µm. The multicore fiber 110 may be made using a Draw-Tower Grating process, although embodiments are not limited thereto. In the cores, at least one Fiber Bragg Grating typically is written. The different cores may have the same type of Fiber Bragg Grating(s) or different types of Fiber Bragg Gratings may be written for different cores.

According to embodiments of the present invention, the optical system furthermore comprises a force transducing element 120. This element may be bendable in one or more directions. The force transducing element typically is fixed to the multicore fiber 110 for transducing force applied to the force transducing element towards the multicore fiber 110, thus resulting into a bending and/or compression and/or tension of the multicore fiber 110.

The force transducing element 120 may be a spring means, although embodiments of the present invention are not limited thereto. In some examples, the spring means may be a compressive spring. In some examples, the spring means may be a tension spring. In yet other examples, the spring means may be a torsion spring.

According to some embodiments of the present invention, the force transducing element 120 may be adapted for allowing a pretension of the fiber 110. In other words, the force transducing element and the multicore fiber 110 may be fixed to each other such that the multicore fiber 110 is under pretension when no external force, external to the force transducer element 120, is applied to the system.

The force transducing element 120 may be fixed to the multicore fiber 110 at two fixation points 130, 132 such that the Fiber Bragg Grating 112 is positioned in between the two fixation points, i.e. such that the force transducing element 120 spans the region of the multicore fiber 110 wherein the Fiber Bragg Grating 112 is positioned. Different Fiber Bragg Gratings 112 used in a same core may have a different wavelength such that identification of their position is possible. The force transducing element 120 may be fixed with any suitable fixing means, such as for example but not limited to glass solder, glue, mechanical fixation, etc.

In other examples, the force transducing element 120 is fixed along a length of the multicore fiber 110, spanning at least the Fiber Bragg Grating 112. The latter may be obtained by applying a glue between the force transducing element 120 and the multicore fiber 110. In some particular examples the glue may have been applied such that the multicore fiber is under pretension.

The stiffness of the force transducing element 120 may be selected such that it dominates, at the location of the force transducing element, the stiffness of the host material whereto the force transducing element is attached or wherein the force transducing element is integrated. Where reference is made to the stiffness, reference is made to at least one of the bending stiffness and/or compression stiffness and/or tension stiffness. In some embodiments, reference may be made to a combination of more or all of the bending stiffness, the compression stiffness and the tension stiffness.

The force transducing element properties also may be selected or adapted for obtaining or tuning the appropriate force sensitivity in a lateral direction, a longitudinal direction or a lateral and/or longitudinal direction for a given multicore fiber 110.

According to embodiments of the present invention, the multicore fiber 110 is connectable or is connected to a measurement system 140 for optically measuring the response of at least one Fiber Bragg Grating 112, for each of at least 2 cores of the multicore fiber 110, as a result of the multicore fiber 110 bending and/or compression and/or tension. This optically measuring of the response typically may be used for deriving a characteristic of the force inducing the bending and/or compression and/or tension. This force is acting on the position of the force transducing element 120, or a larger system to which the force transducing element 120, is connected. Such a system may for example be a catheter, although embodiments are not limited thereto.

The measurement system 140 may for example comprise a radiation source and a fan-out for respectively launching a radiation beam in one or more of the cores of the multicore fiber 110 and sensing a reply from the one or more Fiber Bragg Grating. The measurement system 140 may comprise an interrogator. The measurement system 140 also may comprise a processor for running algorithms for data readout and processing.

In one embodiment, the measurement system 140 may be adapted for simultaneous and real-time monitoring of induced optical response (e.g. wavelength shift) in some of the cores of the multicore fiber, e.g. in three or more outer cores of the multicore fiber. Depending on the curvature orientation of the multicore fiber, some of the Fiber Bragg Gratings on the outer cores will experience a relative longitudinal tension or compression with respect to the central core and therefore, will register different optical responses.

To calculate the force, the optical responses (e.g. relative strains and/or wavelength shifts) are measured, processed, and analyzed.

In one embodiment, the multicore fiber may furthermore comprise at least one Fiber Bragg Grating positioned away from the force transducing element for determining based thereon a shape and/or curvature of the multicore fiber outside the force transducing element.

The measurements of the optical responses may be performed using well-established detection schemes such as for example wavelength division multiplexing and optical frequency domain reflectometry. The system according to embodiments of the present invention may be suitable for a large variety of applications, e.g. for force sensing in ablation catheters, biopsy and brachytherapy and delivery of compounds.

In one aspect, the present invention relates to a medical system comprising an optical system according to an embodiment as described in the first aspect. The medical system may for example be an introducer, a catheter, a needle, a laparoscope, an endoscope and a robotic arm with a rigid or flexible shaft.

In yet another aspect, the present invention relates to the use of an optical system for sensing a force on an optical system on the position of a force transducing element or on a medical system comprising this part of the optical system.

In some embodiments, the present invention also relates to use of a system as described above for measuring a contact force. The latter may for example be used in medical applications, although embodiments are not limited thereto and may also be used in e.g. mechanical applications.

The invention claimed is:

1. An optical system, the optical system being connected or connectable to a host material comprising structural elements, the optical system comprising:
    a multicore fiber comprising at least two cores of which each core comprises at least one Fiber Bragg Grating,
    a force transducing element being bendable in one or more directions and being fixed to the multicore fiber so as to transduce force applied to the force transducing element to the multicore fiber, resulting into a bending and/or compression and/or tension of the multicore fiber at a position of the at least one Fiber Bragg Grating, wherein the multicore fiber being connectable or connected to a measurement system for optically measuring the response of the at least one Fiber Bragg Grating, for each of at least 2 cores of the multicore fiber, as a result of the multicore fiber bending and/or compression and/or tension for deriving a characteristic of the force acting on a position of the force transducing element of the optical system, wherein, at a location of the force transducing element, a bending stiffness of the optical system is selected to be more dominant than a bending stiffness of the host material, the bending stiffness at the location of the force transducing element thereby being substantially independent of structural elements surrounding the fiber and the force transducing element.

2. The optical system according to claim 1, wherein the force transducing element is a spring means.

3. The optical system according to claim 2, wherein the force transducing element is a compressive spring means.

4. The optical system according to claim 1, wherein the optical system, at the position of the force transducing element does not have one or more preferential bending directions imposed by the force transducing element.

5. The optical system according to claim 1, wherein the force transducing element and the multicore fiber are fixed to each other such that the multicore fiber is under pretension when no external force, external to the optical system, is applied to the force transducing element.

6. The optical system according to claim 1, wherein the force transducing element is fixed to the multicore fiber at two fixation points such that the at least one Fiber Bragg Grating is positioned on the multicore fiber in between the two fixation points or wherein the force transducing element is fixed along a length of the multicore fiber spanning the at least one Fiber Bragg Grating.

7. The optical system according to claim 1, wherein the force transducing element properties are adapted for obtaining/tuning an appropriate force sensitivity in a lateral and/or longitudinal direction for a given multicore fiber.

8. The optical system according to claim 1, the optical system comprising said measurement system.

9. The optical system according to claim 8, wherein the measurement system is configured for performing a calibration step whereby information regarding a status of the at least one Fiber Bragg Grating in the multicore fiber is obtained prior to an external force being applied.

10. The optical system according to claim 1, wherein the optical system is a force sensing system.

11. The optical system according to claim 1 wherein the multicore fiber is a twisted multicore fiber having a center core and twisted outer cores inside a cladding, whereby the measurement system is adapted for discriminating between temperature and longitudinal force influences acting on the optical system, at the position of the force transducing element.

12. The optical system according to claim 1,
whereby the force transducing element is adapted such that it is highly resistant against torsion or
wherein the force transducing element is a rotation spring for further inducing a twist to the multicore fiber when an external longitudinal force is induced and
wherein the measurement system is adapted for discriminating between temperature and longitudinal force influences acting on the optical system at the position of the force transducing means.

13. The optical system according to claim 1, wherein the measurement system is adapted for deriving a torsion of the multicore fiber and/or force transducing element.

14. The optical system according to claim 1, wherein the at least one Fiber Bragg Grating is positioned inside a multicore fiber having a preferential twist even if no external force is applied or present.

15. The optical system according to claim 1, wherein the optical system or parts thereof are embedded in the host material,
wherein the host material is adapted for preventing or limiting twisting of the optical system at the position of the force transducing element, when an externally induced torsion force is applied to the host material.

16. The optical system according to claim 1, wherein the multicore fiber furthermore comprises at least one Fiber Bragg Grating positioned away from the force transducing element for determining based thereon a shape and/or curvature of the multicore fiber outside the force transducing element.

17. A medical device comprising an optical system according to claim 1, wherein the optical system provides force information regarding force applied on the medical device.

18. The medical device according to claim 17, the medical device being any of a catheter, an introducer, a needle, a laparoscope, an endoscope, or a robotic arm.

* * * * *